United States Patent [19]

Horn

[11] Patent Number: 4,898,475
[45] Date of Patent: Feb. 6, 1990

[54] APPARATUS AND METHOD FOR THE MEASURING OF DEW POINTS

[75] Inventor: Petr Horn, Samstagern, Switzerland

[73] Assignee: Novasina AG, Pfaffikon, Switzerland

[21] Appl. No.: 167,975

[22] Filed: Mar. 14, 1988

[30] Foreign Application Priority Data

Mar. 16, 1987 [CH] Switzerland .................. 1058/87

[51] Int. Cl.$^4$ ............................ G01N 25/68
[52] U.S. Cl. ................................ 374/28; 374/21
[58] Field of Search ............... 374/15, 21, 20, 27, 374/28, 16, 25; 333/23, 24, 34, 35; 361/286

[56] References Cited

U.S. PATENT DOCUMENTS

| | | | |
|---|---|---|---|
| 2,680,371 | 6/1954 | Donath | 374/28 |
| 2,904,995 | 9/1959 | Obermaier | 374/28 |
| 3,396,574 | 8/1968 | Hanlein et al. | 374/28 |
| 3,930,398 | 1/1976 | Levina et al. | 374/21 |
| 4,276,768 | 7/1981 | Dadachanji | 374/28 |
| 4,579,462 | 4/1986 | Rall et al. | 374/28 |
| 4,626,774 | 12/1986 | Regtien | 374/28 |

FOREIGN PATENT DOCUMENTS

| | | | |
|---|---|---|---|
| 3446277 | 12/1984 | Fed. Rep. of Germany | 374/28 |
| 2295477 | 8/1976 | France | |
| 709988 | 1/1980 | U.S.S.R. | 374/28 |
| 1117515 | 7/1989 | U.S.S.R. | 374/15 |

*Primary Examiner*—William A. Cuchlinski, Jr.
*Assistant Examiner*—Jeffrey J. Hohenshell
*Attorney, Agent, or Firm*—Charles E. Brown; Charles A. Brown

[57] ABSTRACT

A heat conducting support having electrodes is located in a chiller block. The electrodes form a temperature sensor, a heater electrode and electrodes for the measuring of the conductivity. The electrodes are covered by an electrically insulating layer, which layer limits or defines, respectively, over a length L a bedewable surface. The chiller block is encased in a heat insulation and its temperature is measured by a second temperature sensor. The cross-sectional area of the heat transfer between chiller block and bedewable surface is substantially smaller than the bedewable surface itself. This makes it now possible that the temperature at the bedewable surface during the forming of the condensate is determined substantially by the temperature of the condensate at the bedewable surface such that increasing formation of condensate a plateau is determinable at the dew point temperature.

6 Claims, 2 Drawing Sheets

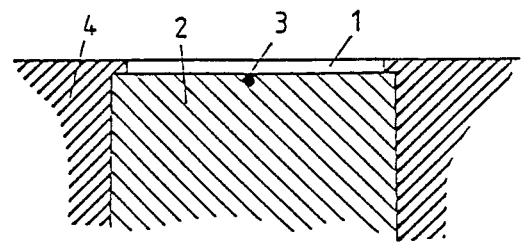
FIG. 1  PRIOR ART
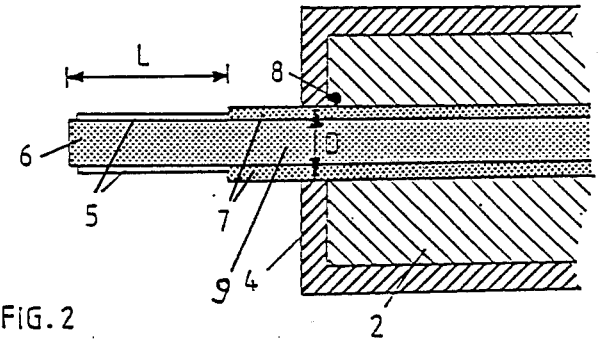 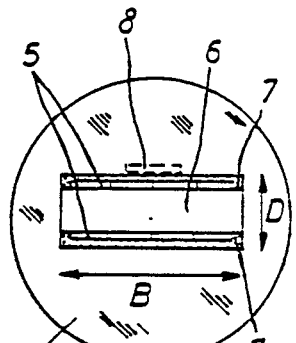
FIG. 2  FIG. 3
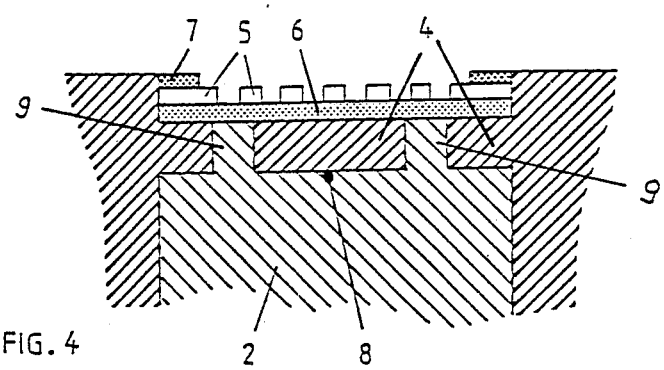
FIG. 4

Fig. 5
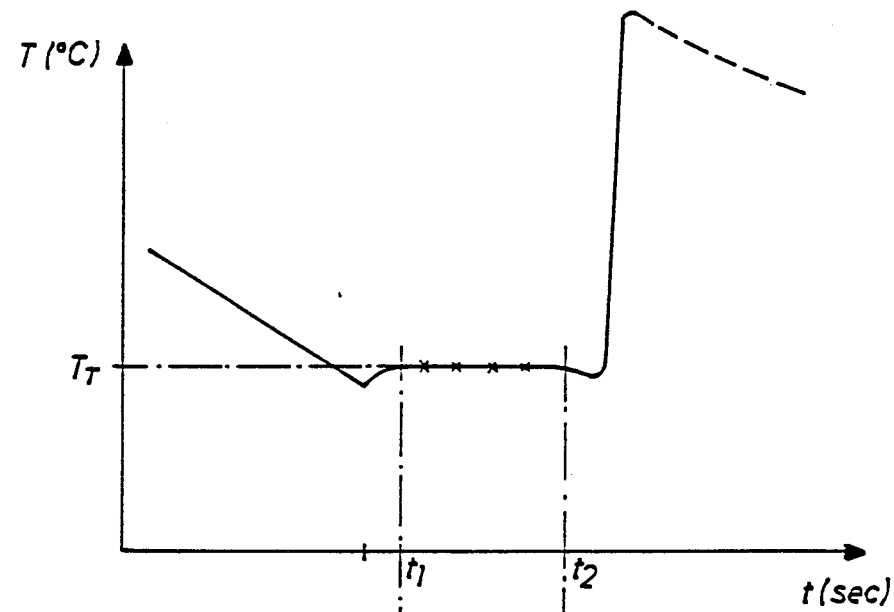
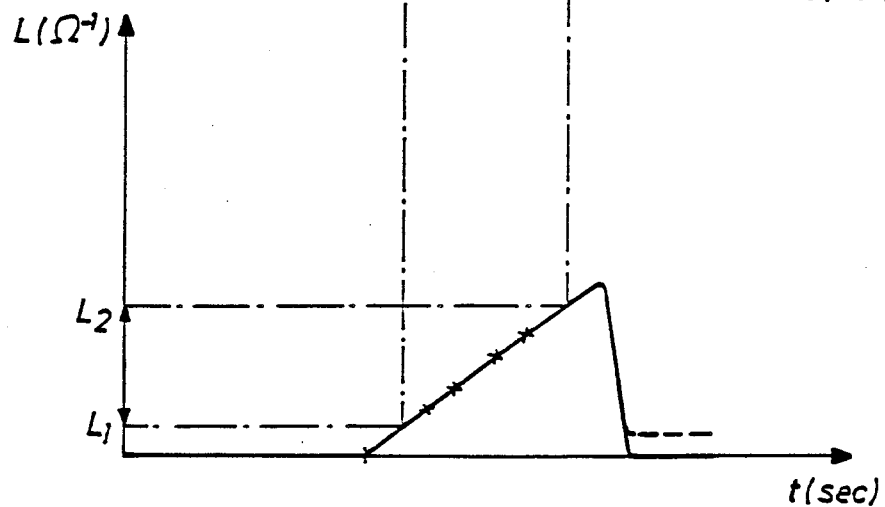
Fig. 6

APPARATUS AND METHOD FOR THE MEASURING OF DEW POINTS

BACKGROUND OF THE INVENTION

1. FIELD OF THE INVENTION

The present invention relates to an apparatus for the measuring of dew points, including a sensor intended to measure a temperature, a chiller block intended for the chilling of a bedewable surface and at least one connecting piece arranged as heat transfer means between chiller block and bedewable surface. The invention relates further to a method of determining dew points.

2. DESCRIPTION OF THE PRIOR ART

A large variety of dew point measuring apparatuses are generally known. Best known is the so-called dew point mirror which includes a mirror polished to a high mirror finish on which the bedewable surface is arranged, whereby the bedewage is detected optically. Such a dew point mirror is disclosed, for instance, in the French publication FR-A-2 044 073. As soon as the bedewage develops, the temperature of the bedewable surface is measured and detected as dew point temperature. The chilling is made by means of a chilling chamber adjoining the dew point mirror including a chilling fluid flowing therethrough. In modern dew point temperature sensors a Peltier element is usually used in the chilling block.

In connection now with dew point mirrors measures have been proposed, allowing an improved visual judging of the time of the bedewage. According to the U.S. publication US-A-2 281 418 the mirror is made to communicate with a chilling element only at its center such that a temperature difference is generated along or over, respectively, such mirror such that the contrast between the initially bedewed area at the center and the other areas of this mirror can be seen clearly. Accordingly, it is exclusively the center of this mirror which acts as bedewable surface.

Apart from mirrors and the accordingly optical recognition or detection, respectively, of the bedewage the bedewing is detected the longer the more by means of electrical signals representing a change of the conductivity, the capacity or the travel time or propagation time, respectively, of acoustical waves. To this end attention is drawn, for instance, to the French publication FR-A 1 128 606. This publication describes, furthermore, that the sensor may be heated by means of a built-in heating element after every measurement made such that the condensate may be removed from the bedewed surface and a subsequent measuring be initiated. Corresponding receiving devices of measuring values are disclosed in the German publications DE-A-3 446 277 and DE-A-1 573 377.

All dew point temperature sensors referred to above include a chilling source, from which the bedewable surface is chilled by heat transmission. Such gives rise to a uncontrollable temperature gradient between the chilling source and the bedewable surface or even on the bedewable surface itself.

Depending on the mechanical arrangement of the temperature sensors the above mentioned uncontrollable temperature gradient between the bedewable surface, the temperature sensor and the chilling source gives rise to a larger or smaller measuring error regarding the dew point temperature. The faster the apparatus is chilled the larger this measuring error grows. Due to a speedy chilling and a large heat transfer from the bedewable surface to the chilling source the bedewable surface is usually undercooled and accordingly an erroneously measure of the dew point temperature is made.

SUMMARY OF THE INVENTION

An object of the present invention is to obviate above drawbacks and to provide an apparatus for measuring dew points which allows an extremely exact measuring of the dew point temperature also in case of a relatively speedy chilling and, additionally, is insensible against contaminations.

A further object is to provide an apparatus for the measuring of dew points, in which the connecting piece arranged as heat transfer means between chiller block and bedewable surface comprises a cross-sectional area which is at least three times less than the bedewable surface, and in which a second sensor intended for measuring the temperature of the chiller block is provided at the chiller block, whereby the temperature gradient between the bedewable surface and the chiller block can be controlled.

A further object of the invention is to provide a method of determining dew points comprising the steps of providing a bedewable surface, a chilling block and a heat transfer means connected between the bedewable surface and the chilling block, and of adjusting the temperature gradient prevailing between the bedewable surface and said chiller block such that the transfer through the heat transfer means attains at the dew point temperature a value which substantially corresponds to the heat of wetting of the condensate forming itself at the surface to be bedewed.

Yet a further object of the invention is to provide a method of measuring dew points by an apparatus which includes a sensor intended to measure a temperature, a chilling block intended for the chilling of a bedewable surface and at least one connecting piece arranged as heat transfer means between the chiller block and the bedewable surface, comprising the steps of adjusting the temperature gradient between the bedewable surface and the chilling block such that the heat transfer through the heat transfer connecting piece attains at the dew point temperature a value which substantially corresponds to the heat of wetting of the condensate forming itself at the surface to be bedewed.

The stated measures allow to keep the heat flow between the bedewable surface and the chilling block during the bedewing at a predetermined, relatively low value. The heat flow can specifically be chosen such that the heat flowing off through the connecting piece during the bedewing corresponds roughly to the heat which is fed to the bedewed surface by the bedewing heat. Accordingly, it is possible to set at this surface during the bedewing a temperature plateau of a roughly constant value, which value is measured for determining the dew point temperature. Independently thereof the chilling of the bedewable surface down to the dew point temperature may be made rather speedily.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 is a schematical illustration of a known dew point temperature sensor;

FIG. 2 is a schematic illustration of a longitudinal section through a first embodiment of an apparatus for the measuring of dew points structured in accordance with the present invention;

FIG. 3 is a front view of the apparatus illustrated in FIG. 2;

FIG. 4 is a schematic view of a second embodiment of an apparatus for the measuring of dew points structured in accordance with the present invention;

FIG. 5 is a diagram in which the change of the temperature at the bedewable surface is plotted relative to time; and FIG. 6 is a corresponding diagram of the measured conductivity of a conductivity measuring sensor at the surface to be bedewed.

DESCRIPTION OF THE PREFERRED EMBODIMENTS

FIG. 1 illustrates on a schematic basis a known sensor or apparatus, respectively, for the measuring of dew points designed as dew point mirror. The mirror surface 1 provides the bedewable surface and is cooled by a not specifically illustrated chilling block 2 such to generate a bedewing at or of, respectively, the mirror surface 1. The temperature prevailing at the mirror surface 1 is measured by a temperature sensor 3. In order to prevent a bedewing at the chilling block 2 such that the mirror surface 1 is bedewed only, the chiller block 2 is packed into a thermal insulation 4. The chiller block 2 of most of the dew point mirrors consists of a Peltier element having electrical connections, a cold and a warm side and of further chilling bodies, which conduct or transport, respectively, the power loss of the Peltier element away. Multistage Peltier elements have been used quite often. With regard to the explanation of the present invention the illustration is restricted to the final chilling surface immediately ahead of the bedewable surface, whereby here the geometric arrangement is of importance. All other components are of generally known design and known to the person skilled in the prevailing art such that no extensive detailed description thereof is necessary. FIG. 1 discloses that quite obviously the temperature of the bedewable surface, in this specific case of the mirror surface 1, is determined substantially by the temperature of the chiller block 2, because the heat transfer between chiller block 2 and mirror surface 1 operates extremely well. It must be noted specifically that the cross-sectional area regarding the heat transfer (between chiller block 2 and mirror surface 1) is large in relation to the surface measure of the bedewable surface (mirror surface 1). The wetting heat of the condensate which bedews and which is detected already when smallest amounts thereof appear has accordingly in case of the illustrated geometrical arrangement practically no influence on the temperature measured by the temperature sensor 3, it is rather substantially the temperature of the chiller block 2, which is measured as dew point temperature. This is the reason that in most of the technical literature regarding dew point mirrors the chilling speed when moving through the dew point is considered as decisive. If the dew point is crossed too rapidly, the errors of the measurement of the dew point temperature will grow extremely large.

FIG. 2 illustrates schmatically a longitudinal section of a dew point temperature sensor or apparatus for the measuring of dew points, respectively, which is an embodiment of the present invention. A front view is illustrated in FIG. 3. Electrodes 5 are mounted on a heat conducting support 6. The electrodes 5 are designed and arranged such, that they form a temperature sensor, a conductivity sensor and a heating electrode at the surface of the support such as designed in FIG. 3 by corresponding partitioning.

With regard to the design and arrangement of the electrodes reference is made to the published European patent application No. 0 193 015 of the present applicant, which disclosure discloses suitable electrode designs for the person skilled in the art.

At the rear area the electrodes 5 are covered by an electric insulating layer 7, which layer 7 limits the bedewable surface which can be covered by the conductivity measuring over a length L.

The support 6 covered by mentioned layer 7 is held and supported by the chiller block 2. The chiller block 2 is encased by a thermal insulation 4 such that no condensate can form on the chiller block 2 itself. FIGS. 2 and 3 disclose that the heat transfer between chiller block 2 and the bedewable surface proceeds via a connector piece 9, having the thickness D at the rectangular support 6. The relationship of the cross-sectional area ($D \times B$) utilized for the heat transfer relative to the bedewable surface (about $2 \times B \times L$) can be stated to amount to approximately $D/2L$ at the rectangular support 6.

If support 6 of FIG. 2 is considered as rod having a circular cross section and diameter D, mentioned relationship amounts to about $D/4L$.

Practical tests have now revealed that if the bedewable surface is substantially larger than the cross-sectional area of the heat transport to the chiller block 2, at the time or instance, respectively, of the bedewing the temperature of the surface is governed substantially by the bedewing heat of the condensate. By means of this geometrical relationships it is possible to determine at a constant chilling of the chiller block 2 a plateau at the dew point temperature such as will be explained later based on FIGS. 5 and 6, whereby the measured conductivity at the bedewable surface and accordingly the amount of condensate increases continuously. This allows now an extremely precise and reproducible measuring of the dew point temperature.

In the embodiment according to FIGS. 2 and 3 mentioned dimensions amount to about: $L=6$ mm, $D=0.8$ mm, such that the relation cross-sectional area to bedewable surface is in the range between 1 to 7 and 1 to 8.

Apart from the cross-sectional area of the connecting piece 9 the heat transport depends also on the temperature gradient which is present in the support 6 or in the connecting piece 9, respectively, if the bedewable surface is initially heated and thereafter chilled by means of the chiller block 2.

For verification and consideration of the temperature gradient formed in the support 6 by the heat transfer, a second temperature sensor 8 is located at the edge of the chiller block 2. Based on the temperature values of the first and of the second temperature sensor it is possible to determine the temperature gradient and accordingly the heat flow in the support. The temperature of the chiller block can then be selected such that during the bedewing the mentioned balance of the heat added and removed is arrived at at the bedewable surface.

By heating the bedewable surface it is possible to evaporate the condensate very speedily and to let the bedewable surface chill very speedily after switching the heating off if the chiller block 2 is held below the dew point temperature and has a considerably larger mass then the support 6 projecting out of the chiller block 2. Practical runs have revealed that this process can be repeated within a few seconds, a time span which amounts by commonly available dew point mirrors to several minutes.

In FIGS. 5 and 6 this process is plotted schematically. FIG. 5 illustrates a diagram of the temperature T measured at the bedewable surface in function of time and FIG. 6 illustrates the measured conductivity L at the conductivity sensor which is a measure for the amount of condensate on the bedewable surface.

Initially, the temperature of the previously heated bedewable surface decreases up to about the dew point $T_T$. Together with the beginning of the bedewing a temperature plateau is generated such as mentioned above. As soon as a specific minimum of the bedewage is arrived at, which is determinable by a conductivity threshold $L_1$, the temperature values are taken up until a higher conductivity threshold $L_2$. Thereafter the bedewable surface is heated such that the condensate evaporates and a new measuring cycle can begin.

A further advantage of the geometrical arrangement of FIG. 2 is that upon a detecting of a soiling at the bedewable surface which in spite of the heating can be measured substantially above the dew point or environment temperature, respectively, by the measuring of the conductivity or other above described measurements, it is possible to heat the bedewable surface up to more than 500° or 600° C., such to burn the respective soiling or dirt off. To this end a conductivity sensor as disclosed in the European patent application No. 0 193 015 can be used advantageously. Such as illustrated in FIG. 6 by a broken line the condition of a soiling can be determined in that the conductivity of the conductivity sensor does not return to substantially zero after a normal heating.

Quite obviously it is also possible to use an optical procedure for the determination of the forming of condensate on the bedewable surface. It is also possible to use a measuring of a change of the capacity or impedance, of the propagation time of acoustical waves or a shifting of the resonance of a mechanical or electrical oscillator (piezo-crystal or quartz) for a determination of the forming of the condensate.

FIG. 4 illustrates a second embodiment of the dew point sensor apparatus structured in accordance with the invention. The chiller block 2 adjoins a support 6 having electrodes 5 which form a temperature sensor, a heating electrode and electrodes for measuring of the conductivity. The electrodes 5 are covered by a layer 7, such to limit the bedewable surface. The chiller block 2 is encased by a heat insulation 4. A second temperature sensor 8 is located in the chiller block 2 allowing a measuring of its temperature. In this embodiment a section through a dew point temperature sensor is designed without indicating in detail designs of the connections to the electrodes and to the chiller block 2, and the chiller block 2 or the support 6 may be rectangular or circular. FIG. 4 discloses that the cross-sectional area of the connector piece 9 operative for the heat transfer between chiller block 2 and bedewable surface at which the electrodes 5 are located is substantially smaller than the bedewable surface.

The function or operation, respectively, of the dew point temperature sensor illustrated in FIG. 4 is substantially the same as disclosed already with regard to the description of the embodiment illustrated in FIG. 2. Also here all possibilities for recognizing or determining, respectively, the forming of the condensate as referred to in FIG. 2 are available.

While there are shown and described present preferred embodiments of the invention, it is to be distinctly understood that the invention is not limited thereto, but may be otherwise variously embodied and practiced within the scope of the following claims.

I claim:

1. An apparatus for the measuring of dew points, including a first sensor intended to measure a temperature, a chiller block intended for the chilling of a bedewable surface having an area and at least one connecting piece arranged as heat transfer means between said chiller block and said bedewable surface, in which said connecting piece comprises a two ended member made of thermoconductive material, said member being at one end in thermal contact with said chiller block and at the other end in thermal contact with said bedewable surface, and comprising a cross-sectional area for heat transfer between the two ends of said connecting piece, said cross-sectional area being at least three times less than the total area of the bedewable surface, and in which said first sensor is provided at or adjacent to said bedewable surface, whereas a second sensor intended for measuring the temperature of the chiller block is provided at said chiller block, whereby the temperature gradient along said member between said bedewable surface and said chiller block can be controlled.

2. The apparatus as claimed in claim 1, in which said second sensor is located at said one end of said member, which is in thermal contact with said chiller block.

3. The apparatus as claimed in claim 1, comprising further electrodes intended for a measuring of the conductivity at said bedewable surface.

4. The apparatus as claimed in claim 3, comprising further an insulation layer which limits said bedewable surface and electrically insulates said electrodes.

5. The apparatus as claimed in claim 1, comprising further at least one heating electrode at said bedewable surface.

6. The apparatus as claimed in claim 5, comprising further an insulation layer which limits said bedewable surface and electrically insulates said electrodes.

* * * * *